United States Patent
Sakuragi

(10) Patent No.: US 10,524,823 B2
(45) Date of Patent: Jan. 7, 2020

(54) SURGERY ASSISTANCE APPARATUS, METHOD AND PROGRAM

(71) Applicant: FUJIFILM Corporation, Tokyo (JP)

(72) Inventor: Futoshi Sakuragi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 568 days.

(21) Appl. No.: 14/601,439

(22) Filed: Jan. 21, 2015

(65) Prior Publication Data

US 2015/0133764 A1 May 14, 2015

Related U.S. Application Data

(63) Continuation of application No. PCT/JP2013/004235, filed on Jul. 9, 2013.

(30) Foreign Application Priority Data

Jul. 24, 2012 (JP) .................................. 2012-163500

(51) Int. Cl.
*A61B 17/3205* (2006.01)
*A61B 6/03* (2006.01)
(Continued)

(52) U.S. Cl.
CPC .......... *A61B 17/3205* (2013.01); *A61B 5/055* (2013.01); *A61B 5/489* (2013.01); *A61B 6/032* (2013.01); *A61B 6/504* (2013.01)

(58) Field of Classification Search
CPC ................ A61B 17/3205; A61B 19/50; A61B 2017/00809; A61B 2034/105;
(Continued)

(56) References Cited

U.S. PATENT DOCUMENTS

| 5,715,836 A | 2/1998 | Kliegis et al. |
| 7,058,210 B2 | 6/2006 | Mundy et al. |

(Continued)

FOREIGN PATENT DOCUMENTS

| EP | 2 422 736 A2 | 2/2012 |
| JP | 8-509393 A | 10/1996 |

(Continued)

OTHER PUBLICATIONS

Reitinger et al., "Liver surgery planning using virtual reality". IEEE Computer Graphics and Applications, Nov./Dec. 2006, pp. 36-47.*

(Continued)

*Primary Examiner* — Katherine L Fernandez
*Assistant Examiner* — Yi-Shan Yang
(74) *Attorney, Agent, or Firm* — Sughrue Mion, PLLC

(57) ABSTRACT

When an image representing an organ in which an excision region has been identified in such a manner that a blood vessel region in the organ is visually recognizable is generated from a three-dimensional image of the organ, an input specifying a depth of cutting is received, and a portion of a boundary surface within the specified depth of cutting along the boundary surface from an outer edge of the boundary surface toward an inside is determined as a cutting surface, and the boundary surface being between the excision region and a non-excision region in the organ. The image representing the organ in such a manner that only a partial blood vessel region, which is present in a neighborhood region of the cutting surface in the blood vessel region of the organ, is visually recognizable is generated from the three-dimensional image.

17 Claims, 5 Drawing Sheets

(51) Int. Cl.
*A61B 6/00* (2006.01)
*A61B 5/055* (2006.01)
*A61B 5/00* (2006.01)

(58) Field of Classification Search
CPC ... A61B 2034/107; A61B 34/10; A61B 5/004; A61B 5/055; A61B 5/489
See application file for complete search history.

(56) References Cited

U.S. PATENT DOCUMENTS

| | | | |
|---|---|---|---|
| 2004/0152970 A1* | 8/2004 | Hunter | A61B 17/025 600/424 |
| 2005/0215854 A1 | 9/2005 | Ozaki et al. | |
| 2006/0279568 A1 | 12/2006 | Matsumoto | |
| 2008/0103385 A1* | 5/2008 | Ma | G06T 7/0012 600/416 |
| 2010/0316268 A1* | 12/2010 | Liang | G06T 19/00 382/128 |
| 2012/0053443 A1 | 3/2012 | Sakuragi | |
| 2013/0144160 A1 | 6/2013 | Sakuragi | |

FOREIGN PATENT DOCUMENTS

| | | |
|---|---|---|
| JP | 2003-33349 A | 2/2003 |
| JP | 2003-225231 A | 8/2003 |
| JP | 2003-271924 A | 9/2003 |
| JP | 2005-278888 A | 10/2005 |
| JP | 2006-346022 A | 12/2006 |
| JP | 2008-167793 A | 7/2008 |
| JP | 2011-10828 A | 1/2011 |
| JP | 2011010828 A * | 1/2011 |
| JP | 2012-34988 A | 2/2012 |
| WO | 2010/132606 A1 | 11/2010 |

OTHER PUBLICATIONS

Koui Miura et al. "Hepatectomy Simulation—Its Fundamentals and Clinical Application", MEDIX 2001, pp. 9-14, vol. 35.
K. Kubota et al., "Evaluation of Computer-Aided Diagnosis system for Lung Cancer based on Helical CT images", Technical Report of IEICE, the Institute of Electronics, Information and Communication Engineers, 2001, pp. 41-46, MI2001-41.
Reinhard Beichel et al., "Liver Segment Approximation in CT Data for Surgical Resection Planning", Medical Imaging 2004: Image Processing, Proceedings of the SPIE 2004, pp. 1435-1446, vol. 5370.
Yuki Wakida et al., "Liver Cancer Detection based on a Temporal Density Feature from Abdominal Dynamic X-ray CT Images", Journal of Computer Aided Diagnosis of Medical Images, Mar. 2007, pp. 1-10, vol. 10, No. 1.
International Search Report for PCT/JP2013/004235 dated Nov. 5, 2013.
Communication dated Sep. 15, 2015 from the Japanese Patent Office issued in corresponding Japanese application No. 2012-163500.
Communication, dated Mar. 23, 2016, from the European Patent Office in counterpart European application No. 13822305.2.
Communication dated Apr. 18, 2017 from the European Patent Office in counterpart European Patent Application No. 13 822 305.2.

* cited by examiner

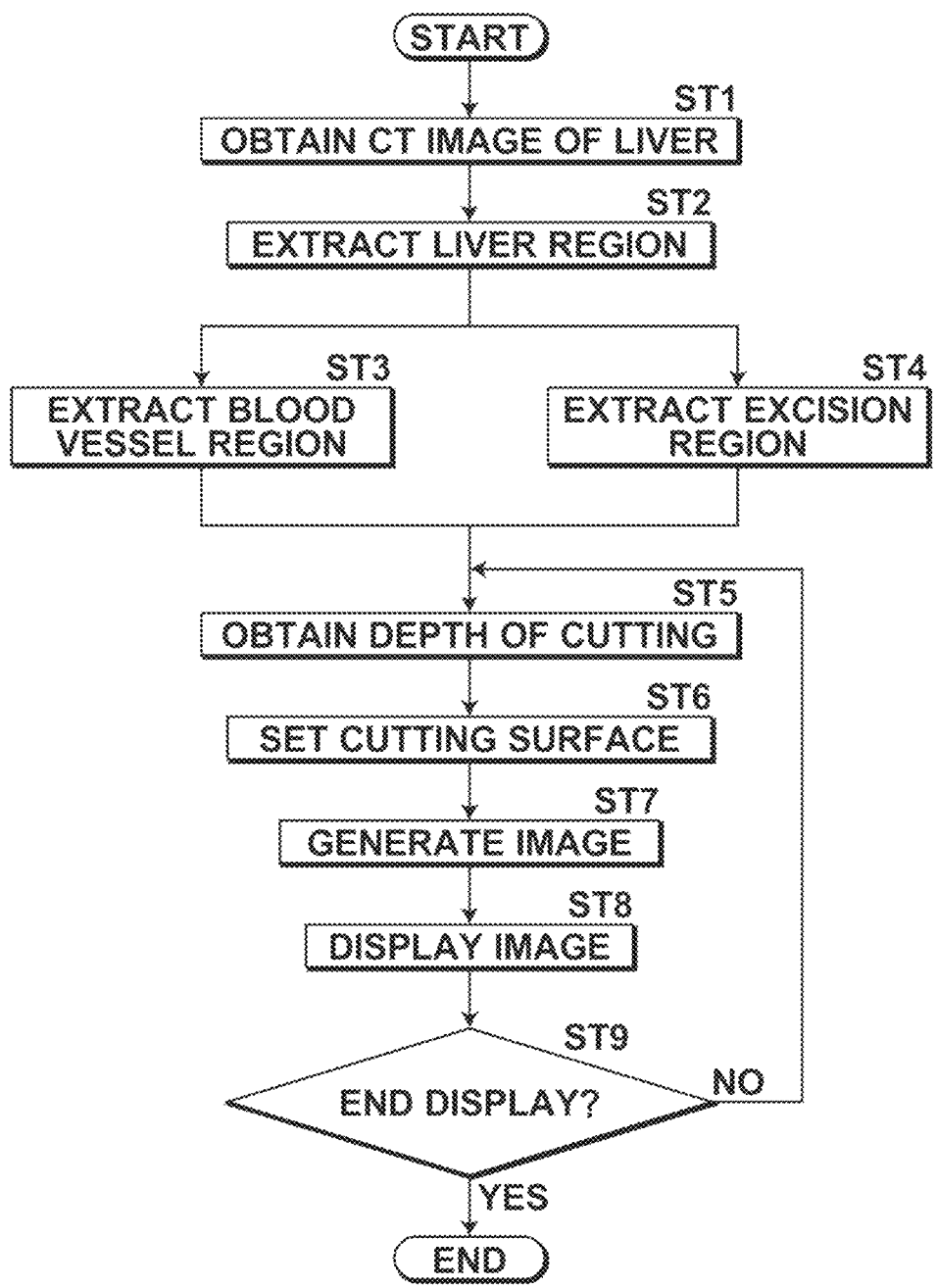

SURGERY ASSISTANCE APPARATUS, METHOD AND PROGRAM

CROSS-REFERENCE TO RELATED APPLICATIONS

This application is a Continuation of PCT International Application No. PCT/JP2013/004235 filed on Jul. 9, 2013, which claims priority under 35 U.S.C. § 119(a) to Japanese Patent Application No. 2012-163500 filed on Jul. 24, 2012. Each of the above applications is hereby expressly incorporated by reference, in its entirety, into the present application.

BACKGROUND OF THE INVENTION

Field of the Invention

The present invention relates to a surgery assistance apparatus, method and program for assisting a doctor who performs an excision surgery on an organ, such as the liver or lungs.

Description of the Related Art

When a surgery is performed to remove a diseased part of an organ, such as the liver or lungs, in recent years, image-based diagnosis is performed before the surgery to determine an appropriate excision region in advance so as to preserve the function of the organ as much as possible.

K. Miura et al., "Hepatectomy Simulation—Its Fundamentals and Clinical Application—", MEDIX, Vol. 35, pp. 9-14, 2001 (Non-Patent Document 1) proposes a technique for generating and providing a three-dimensional image of the liver, in which 3D images of a liver parenchyma, a tumor region, a portal vein and hepatic veins are integrated, in such a manner that an excision region and a region that is kept without being excised (a non-excision region) are not displayed or are displayed in an opaque manner while blood vessel regions included in the regions are made visually recognizable. The technique makes it possible to check, in advance, the condition of blood vessel branches to be treated during surgery on a surface along which cutting is to be performed, i.e., a cutting surface.

SUMMARY OF THE INVENTION

Meanwhile, in actual surgeries, a position slightly different from a cutting surface that was determined in a simulation before the surgery is sometimes cut because of a visual field in the surgery, the condition of the organ, various factors that were not predictable in the simulation before the surgery, the technical level of a surgeon who operates, and the like. Therefore, it is necessary to check the course of blood vessels in the neighborhood of the cutting surface in advance. Further, when a different position is cut, and an unpredicted blood vessel appears during the surgery, the course of blood vessels in the neighborhood of the cutting surface needs to be checked to immediately distinguish and identify the blood vessel.

However, in the related technique as described above, all of the blood vessel regions included in the excision region and the non-excision region are uniformly displayed. Therefore, it is difficult to immediately identify and check a part of the blood vessel regions in which the surgeon has an interest.

In view of the foregoing circumstances, it is an object of the present invention to provide a surgery assistance apparatus, method and program that provides an image appropriate for observation of the course of blood vessels in the neighborhood of a cutting surface.

A surgery assistance apparatus of the present invention includes an image generation means that generates, from a three-dimensional image of an organ in which an excision region has been identified, an image representing the organ in such a manner that a blood vessel region in the organ is visually recognizable, a depth input receiving means that receives an input specifying a depth of cutting, and a cutting surface setting means that determines, as a cutting surface, a portion of a boundary surface within the specified depth of cutting along the boundary surface from an outer edge of the boundary surface toward an inside, and the boundary surface being between the excision region and a non-excision region, which is a region other than the excision region, in the organ. Further, the image generation means generates, from the three-dimensional image, the image representing the organ in such a manner that only a partial blood vessel region, which is present in a neighborhood region of the cutting surface in the blood vessel region of the organ, is visually recognizable.

In the surgery assistance apparatus of the present invention, the neighborhood region of the cutting surface may be a region the width of which in a direction perpendicular to the cutting surface increases from an inner edge of the cutting surface toward the outer edge of the cutting surface.

Further, the neighborhood region of the cutting surface may have a first width that has been set in advance in a direction perpendicular to the cutting surface at the inner edge of the cutting surface and a second width that has been set in advance in a direction perpendicular to the cutting surface at the outer edge of the cutting surface.

Further, the neighborhood region of the cutting surface may be a region having a first width that has been set in advance in a direction perpendicular to the cutting surface at the inner edge of the cutting surface, and the width of which in a direction perpendicular to the cutting surface increases from the inner edge of the cutting surface toward the outer edge of the cutting surface at a ratio that has been set in advance.

The surgery assistance apparatus of the present invention may further include a width input receiving means that receives an input of specifying the first width. Further, the neighborhood region of the cutting surface may have the first width that has been specified in the direction perpendicular to the cutting surface at the inner edge of the cutting surface.

Further, in the surgery assistance apparatus, the neighborhood region of the cutting surface may be present only toward the excision region from the cutting surface, or only toward the non-excision region from the cutting surface.

Further, the manner that only the partial blood vessel region is visually recognizable may be a manner that a parenchyma region in the organ present in the neighborhood region of the cutting surface is not displayed or is displayed at a lower opacity value than the opacity value of the partial blood vessel region. Here, the parenchyma region means a tissue region that performs the original physiological function of an organ, and refers to a region other than a blood vessel region and a tumor region.

A surgery assistance method of the present invention includes an image generation step of generating, from a three-dimensional image of an organ in which an excision region has been identified, an image representing the organ in such a manner that a blood vessel region in the organ is visually recognizable, a depth input receiving step of receiving an input specifying a depth of cutting, and a cutting surface setting step of determining, as a cutting surface, a portion of a boundary surface within the specified depth of cutting along the boundary surface from an outer edge of the boundary surface toward an inside, and the boundary surface being between the excision region and a non-excision region, which is a region other than the excision region, in the organ. Further, the image generation step is a step of generating, from the three-dimensional image, the image representing the organ in such a manner that only a partial blood vessel region, which is present in a neighborhood region of the cutting surface in the blood vessel region of the organ, is visually recognizable.

A surgery assistance program of the present invention causes a computer to function as an image generation means that generates, from a three-dimensional image of an organ in which an excision region has been identified, an image representing the organ in such a manner that a blood vessel region in the organ is visually recognizable, a depth input receiving means that receives an input specifying a depth of cutting, and a cutting surface setting means that determines, as a cutting surface, a portion of a boundary surface within the specified depth of cutting along the boundary surface from an outer edge of the boundary surface toward an inside, and the boundary surface being between the excision region and a non-excision region, which is a region other than the excision region, in the organ. Further, the image generation means generates, from the three-dimensional image, the image representing the organ in such a manner that only a partial blood vessel region, which is present in a neighborhood region of the cutting surface in the blood vessel region of the organ, is visually recognizable.

According to the surgery assistance apparatus, method and program of the present invention, when the surgery assistance apparatus, method and program generates an image representing an organ in which an excision region has been identified from a three-dimensional image of the organ in such a manner that a blood vessel region in the organ is visually recognizable, an input specifying a depth of cutting is received. Further, the surgery assistance apparatus, method and program determines, as a cutting surface, a portion of a boundary surface within the specified depth of cutting along the boundary surface from an outer edge of the boundary surface toward an inside, and the boundary surface being between the excision region and a non-excision region, which is a region other than the excision region, in the organ. Further, the surgery assistance apparatus, method and program generates, from the three-dimensional image, the image representing the organ in such a manner that only a partial blood vessel region, which is present in a neighborhood region of the cutting surface in the blood vessel region of the organ, is visually recognizable. Therefore, when observation is performed by paying attention to the course of blood vessels in the neighborhood of the cutting surface, it is possible to provide an image appropriate for observation in which only a portion of the whole blood vessel region to which attention is paid in observation is displayed.

In the surgery assistance apparatus, method and program of the present invention, when the neighborhood region of the cutting surface is a region the width of which in a direction perpendicular to the cutting surface increases from an inner edge of the cutting surface toward the outer edge of the cutting surface, it is possible to provide an image in which it is possible to easily observe the course of blood vessels also at a deep position even if the depth of cutting becomes deep.

Further, in the surgery assistance apparatus of the present invention, when the neighborhood region of the cutting surface is present only toward the non-excision region from the cutting surface, it is possible to provide an image appropriate for observation of blood vessels located toward the non-excision region of the cutting surface, and to which special attention needs be paid so as not to damage.

BRIEF DESCRIPTION OF THE DRAWINGS

FIG. 11 is a flowchart for explaining the action of the surgery assistance system.

DESCRIPTION OF THE PREFERRED EMBODIMENTS

Next, an embodiment of a surgery assistance apparatus, method and program of the present invention will be described with reference to drawings. In the embodiment of the present invention, a surgery assistance system that can provide a pseudo cut-state image representing an organ, such as the liver or lungs, before or during a surgery of excising a partial region of the organ will be described. In the surgery assistance system, the set value of depth of cutting (the amount of cutting) is gradually increased as if the organ is cut gradually deeper along a surface to be cut in actual surgeries, and the pseudo-image representing the organ in a state in which the organ is cut at the depth of cutting is provided. The image represents the organ in such a manner that only partial blood vessel region VP, which is present in neighborhood region AR of cutting surface CP (a portion of the entire surface to be cut, and the portion having been cut at the depth of cutting) in blood vessel region V of the organ, is visually recognizable.

Figure 1:
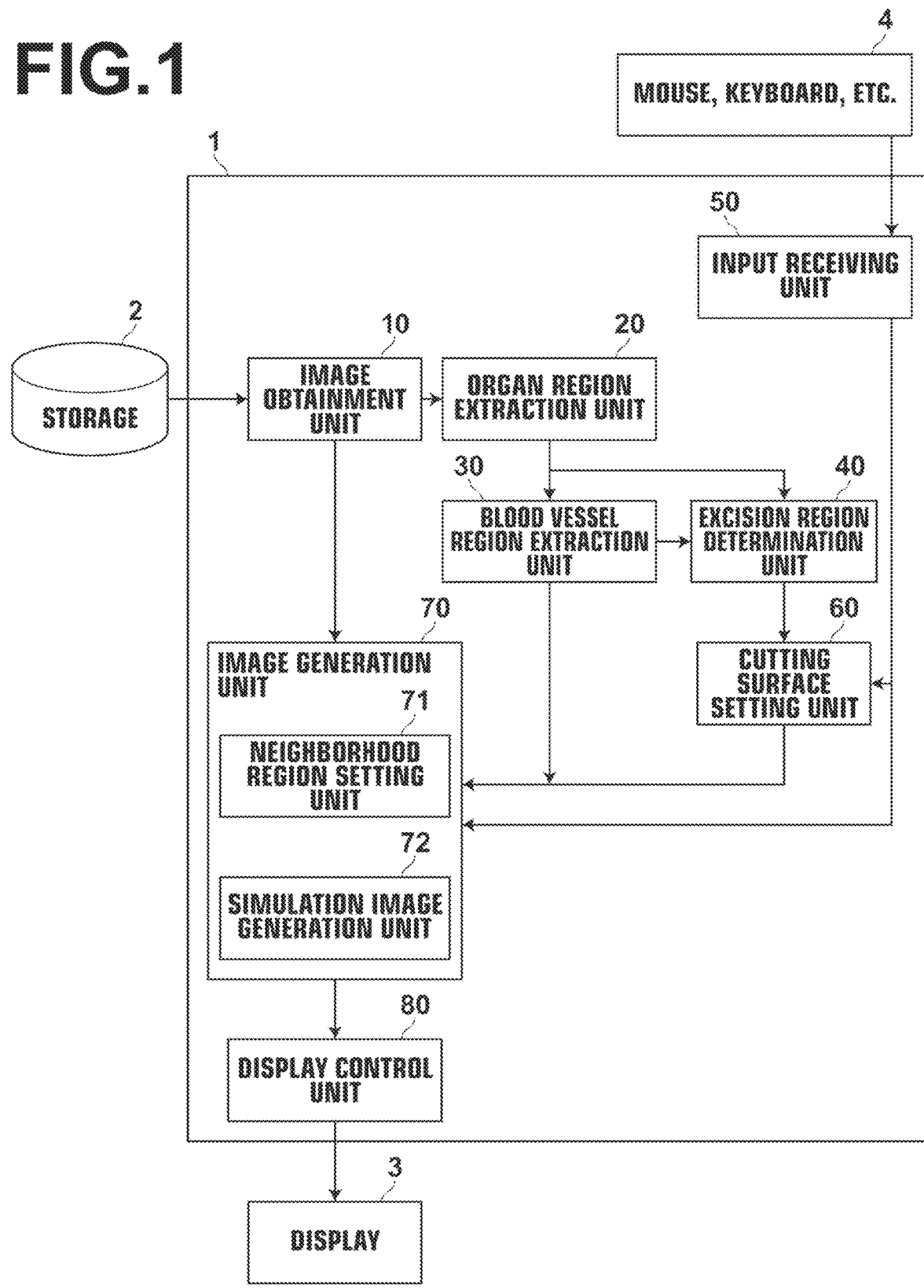
FIG. 1 is a schematic block diagram illustrating the configuration of a surgery assistance system.

FIG. 1 is a schematic diagram illustrating the configuration of a surgery assistance system according to an embodiment of the present invention. A surgery assistance apparatus 1 is a computer in which an embodiment of a surgery assistance program of the present invention has been installed. The computer may be a workstation or a personal computer directly operated by a doctor who makes a diagnosis. Alternatively, the computer may be a server computer connected to the workstation or the personal computer through a network. The surgery assistance program is distributed by being stored in a recording medium, such as a DVD and a CD-ROM, and installed in a computer from the recording medium. Alternatively, the surgery assistance program is stored in a recording device of a server computer connected to a network or in a network storage in an accessible manner from the outside. The surgery assistance program is downloaded and installed in a computer used by a doctor upon request.

The surgery assistance apparatus 1 includes a CPU, a memory and the like. Further, a storage 2, a display 3 and an input device 4, such as a mouse and a keyboard, are connected to the surgery assistance apparatus 1. A surgery assistance program and data (processing parameters, and the like) referred to by the surgery assistance program have been stored in the memory. The surgery assistance program defines, as processing performed by the CPU, image obtainment processing, organ region extraction processing, blood vessel region extraction processing, excision region extraction processing, input receiving processing, cutting surface setting processing and image generation processing. When the CPU executes these kinds of processing in accordance with the program, the computer functions as an image obtainment unit 10, an organ region extraction unit 20, a blood vessel region extraction unit 30, an excision region determination unit 40, an input receiving unit 50 (a depth input receiving means and a width input receiving means), a cutting surface setting unit 60 (a cutting surface setting means), an image generation unit 70 (an image generation means) and a display control unit 80, as illustrated in FIG. 1.

The storage 2 stores, as a three-dimensional image, volume data reconstructed from slice data that have been output from a CT (Computed Tomography) apparatus or an MRI (Magnetic Resonance Imaging) apparatus, volume data output from an MS (Multi Slice) CT apparatus or a cone beam CT apparatus, and the like.

The image obtainment unit 10 obtains a three-dimensional image representing an organ including a diseased part to be excised. In the embodiment of the present invention, an X-ray CT image obtained by imaging the liver of a patient to be examined is used as an image to be processed. The image obtainment unit 10 loads the three-dimensional image that was imaged in advance and stored in the storage 2 into the memory.

The organ region extraction unit 20 extracts an organ region from the three-dimensional image obtained by the image obtainment unit 10. The organ region extraction unit 20 calculates, with respect to the value of each voxel data constituting the three-dimensional image, a feature value representing the likelihood of the contour of the liver. Further, the organ region extraction unit 20 evaluates the calculated feature value based on an evaluation function obtained in advance by machine learning. Accordingly, the organ region extraction unit 20 judges whether the voxel data represent the contour of the liver. The organ region extraction unit 20 extracts voxel data representing the contour of the entire liver by repeating this judgment. In the embodiment of the present invention, an AdaBoost algorithm is used to obtain the evaluation function. A liver region may be extracted by using various known methods as long as the organ is able to be extracted. Other machine learning methods and statistical analysis methods, for example, such as a linear discriminant method, a neural network and a support vector machine may be used.

The blood vessel region extraction unit 30 extracts blood vessel region V from the organ region extracted by the organ region extraction unit 20. First, a linear structure is probed by calculating eigenvalues of 3×3 Hessian matrix for each local region in the liver region 5. One of the three eigenvalues of the Hessian matrix is a value close to zero, and the other two eigenvalues are relatively large values in a region including a linear structure. Further, an eigenvector corresponding to the eigenvalue close to zero represents the main axial direction of the linear structure. The blood vessel region extraction unit 30 utilizes this relationship, and judges the likelihood of a linear structure, based on the eigenvalues of the Hessian matrix, for each local region. Further, when a linear structure is identified in a local region, a center point of the local region is detected as a candidate point.

Further, candidate points detected by probing are connected to each other based on a predetermined algorithm. Accordingly, a tree structure composed of the candidate points and blood vessel branches (edges) connecting the candidate points to each other is constructed. Coordinate information about the plural candidate points that have been detected, and vector information representing the directions of the blood vessel branches are stored in the memory together with identifiers of the candidate points and the blood vessel branches. Then, the contour of a blood vessel (the outer wall of a blood vessel) is identified for each of the detected candidate points in a cross section perpendicular to the path of the blood vessel. The contour of the blood vessel is identified based on the values of voxels surrounding each of the detected candidate points. The shape is identified by using a known segmentation method, typified by Graph-Cuts. Through the process as described above, information necessary to identify the extracted blood vessel region V is generated, and stored in the memory.

The excision region determination unit 40 extracts an abnormal region from the organ region extracted by the organ region extraction unit 20. Further, the excision region determination unit 40 identifies a portion of blood vessel region V related to the extracted abnormal region, and determines, as an excision region 41, a dominated region in the organ that is dominated by the identified portion of blood vessel region V. The excision region determination unit 40 determines, as a non-excision region 42, the organ region other than the determined excision region 41.

As a method for extracting the abnormal region, for example, a three-dimensional image of an organ may be displayed on the display 3. Further, specification of a region by a user using the input device 4, such as a mouse, may be received, and the specified region may be extracted as the abnormal region. Alternatively, the abnormal region may be automatically extracted by using a known technique. Various known methods may be adopted, as a method for automatically extracting an abnormal region. For example, methods for detecting a lung cancer disclosed in Japanese Unexamined Patent Publication No. 2003-225231, Japanese Unexamined Patent Publication No. 2003-271924, and "K. Kubota et al., "Evaluation of Computer-Aided Diagnosis System for Lung Cancer based on Helical CT Images", the Institute of Electronics, Information and Communication Engineers, Technical Report of the Institute of Electronics, Information and Communication Engineers, MI2001-41, pp. 41-46, 2001" and a method for detecting a liver cancer disclosed in "Y. Wakida et al., "Liver Cancer Detection based on a Temporal Density Feature from Abdominal Dynamic X-Ray CT Images", Proceedings of Japan Society of Computer-Aided Diagnosis of Medical Images, Vol. 10, No. 1, pp. 1-10, 2007", and the like may be used.

As a method for identifying a portion of blood vessel region V related to the abnormal region, for example, blood vessel region V may be displayed on the display 3, and an input of specifying a position on a blood vessel by a user using the input device 4, such as a mouse, may be received. Further, a region extending from the specified position toward a portion of the organ including the abnormal region may be identified as the portion of blood vessel region V. Alternatively, the portion of blood vessel region V may be automatically identified by using a known technique.

As methods for obtaining a dominated region, when the target tissue is, for example, a liver, the dominated region may be obtained by using the following method. Dominated regions of respective blood vessels are identified, as liver segments, by identifying which portion of the region other than the blood vessels in the liver (liver parenchyma and the like) is dominated by which blood vessel by using a Voronoi diagram (please refer to Japanese Unexamined Patent Publication No. 2003-033349, "R. Beichel et al., "Liver Segment Approximation in CT Data for Surgical Resection Planning", Medical Imaging 2004: Image Processing, Proceedings of the SPIE, Vol. 5370, pp. 1435-1446, 2004", and the like).

The input receiving unit 50 receives various kinds of setting, such as depth d of cutting and width (for example, W, W0 and W1) of the neighborhood region of cutting surface CP, by the user through the input device 4, such as a mouse. Specifically, a setting screen for setting the depth of cutting or the like is displayed on the display 3, and an input to the setting screen by the user is received.

Figure 2:
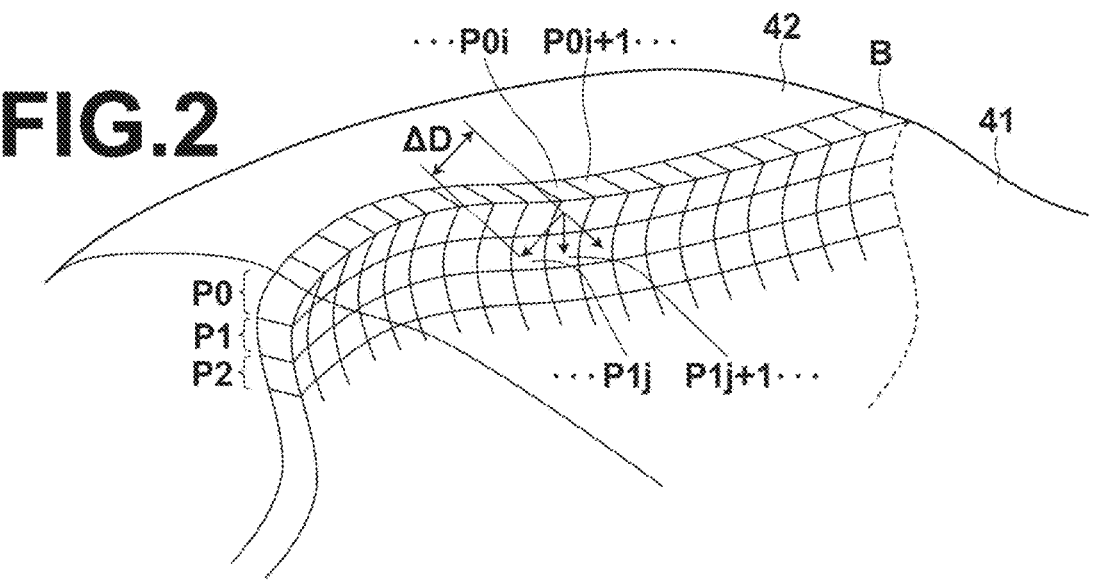
FIG. 2 is a diagram for explaining processing for generating a distance map of a boundary surface.

The cutting surface setting unit 60 sets, as cutting surface CP, a portion of boundary surface B within the range of a depth of cutting along boundary surface B from the outer edge of boundary surface B toward the inside, and boundary surface B is a boundary between an excision region 41 and a non-excision region 42 in the organ region. First, a distance map in which distances are related to all the voxels constituting boundary surface B, respectively, is generated by obtaining, with respect to each of the voxels constituting boundary surface B, a shortest distance along boundary surface B from a voxel constituting the outer edge of boundary surface B. Specifically, as illustrated in FIG. 2, voxel group P0 constituting the outer edge of boundary surface B is extracted. Further, with respect to each voxel P0i (i=1, 2, . . . ) constituting voxel group P0, P1j (∈ voxel group P1) is sequentially detected. P1j is other voxels on boundary surface B that are adjacent to the voxel P0i but not included in voxel group P0. Further, distance ΔD from voxel P0i to detected voxel P1j is obtained, and the obtained distance is stored in such a manner to be related to the voxel P1j. In this case, when the same voxel P1j is detected in detection with respect to two or more different voxels in voxel row P0, i.e., detection overlaps, distance ΔD from each of the two or more voxels is obtained, and a shortest one of the obtained distances is stored in such a manner to be related to the voxel P1j.

Next, with respect to each voxel P1j (j=1, 2, . . . ) constituting voxel group P1, P2k (∈ voxel group P2) is sequentially detected. P2k is other voxels on boundary surface B that are adjacent to the voxel P1j but included neither in voxel group P0 nor in voxel group P1. Further, distance ΔD from voxel P1j to detected voxel P2k is obtained, and the distance stored in such a manner to be related to voxel P1j is added to the obtained distance, and the distance obtained by addition is stored in such a manner to be related to the voxel P2k. In this case, when the same voxel P2k is detected in detection with respect to two or more different voxels of voxel row P1, i.e., detection overlaps, distance ΔD from each of the two or more voxels is obtained, and a shortest one of the obtained distances is stored in such a manner to be related to the voxel P2k. Next, similar processing is performed for voxel group P2, voxel group P3, . . . . Consequently, a distance map in which all the voxels constituting boundary surface B are related to distances is generated.

Then, the cutting surface setting unit 60 refers to the generated distance map, and identifies, among all the voxels constituting boundary surface B, a set of voxels related to distances that are less than or equal to depth d of cutting that has been input by the user and received at the input receiving unit 50. The cutting surface setting unit 60 sets the identified set of voxels, as cutting surface CP.

The image generation unit 70 generates an image (hereinafter, referred to as a simulation image) from the three-dimensional image obtained by the image obtainment unit 10. The simulation image represents an organ in such a manner that only partial blood vessel region VP that is present in neighborhood region AR of cutting surface CP in the whole blood vessel region V of the organ is visually recognizable. The image generation unit 70 includes a neighborhood region setting unit 71, which sets neighborhood region AR of cutting surface CP, and a simulation image generation unit 72, which generates, based on information about the set neighborhood region AR, a simulation image from the three-dimensional image.

Figure 3:
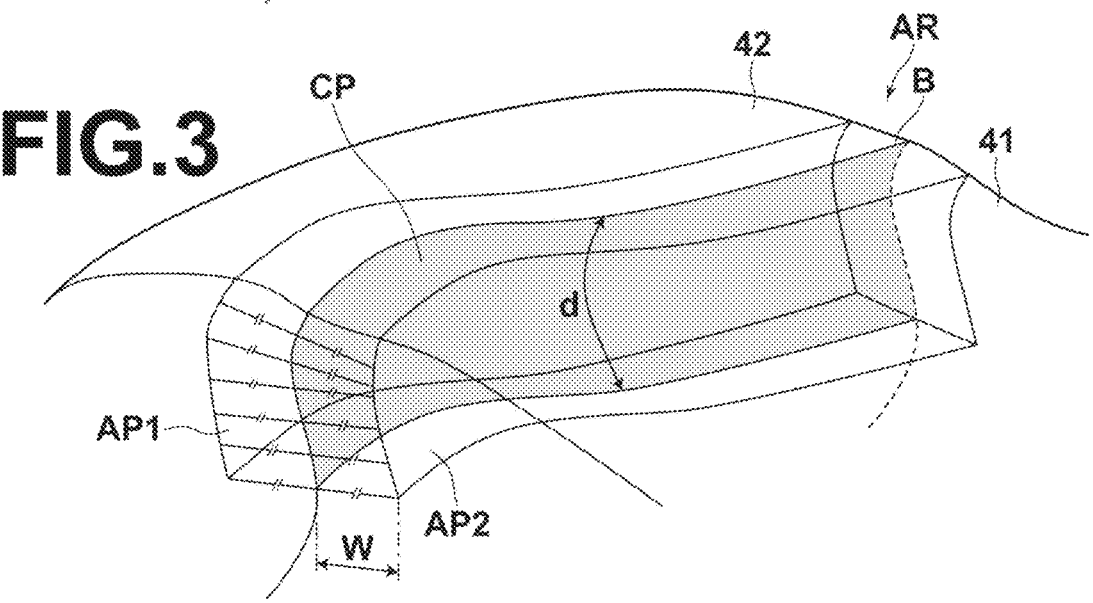
FIG. 3 is a diagram illustrating an example of setting a neighborhood region of a cutting surface.
Figure 4:
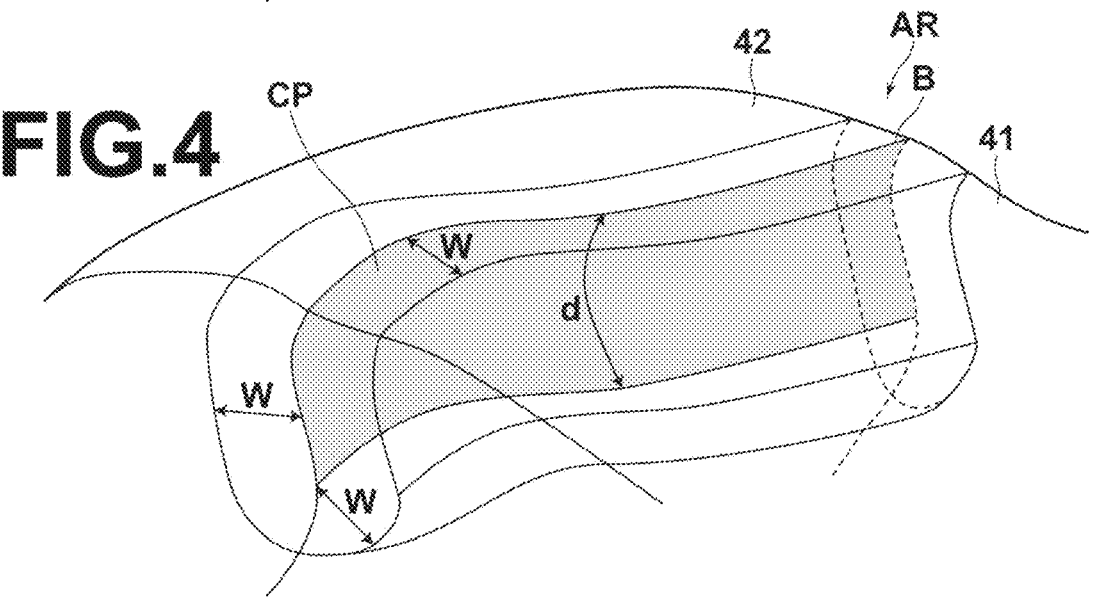
FIG. 4 is a diagram illustrating another example of setting a neighborhood region of a cutting surface.

The neighborhood region setting unit 71 sets, as neighborhood region AR of cutting surface CP, a region with an arbitrary thickness from cutting surface CP toward one of the excision region 41 side and the non-excision 42 side, or toward both of the excision region 41 side and the non-excision 42 side. For example, the neighborhood region setting unit 71 obtains set AP1 of voxels (voxel group AP1) located at positions away from voxels constituting cutting surface CP, respectively, toward the excision region 41 side by width W. Further, the neighborhood region setting unit 71 obtains set AP2 of voxels (voxel group AP2) located at positions away from voxels constituting cutting surface CP, respectively, toward the non-excision region 42 side by the same width W. Further, the neighborhood region setting unit 71 sets, as neighborhood region AR of cutting surface CP, a region including voxel groups AP1 and AP2. As illustrated in FIG. 3, a smallest range of region that includes the voxel groups AP1 and AP2 may be obtained, as the region including voxel groups AP1 and AP2. Alternatively, as illustrated in FIG. 4, a surface (curved surface) having the voxels of voxel groups AP 1 and AP2, as points on its surface, may be obtained by RBF (Radial Basis Function) or by spline surface approximation. Further, a region enclosed by the surface may be obtained, as neighborhood region AR of cutting surface CP.

Figure 5:
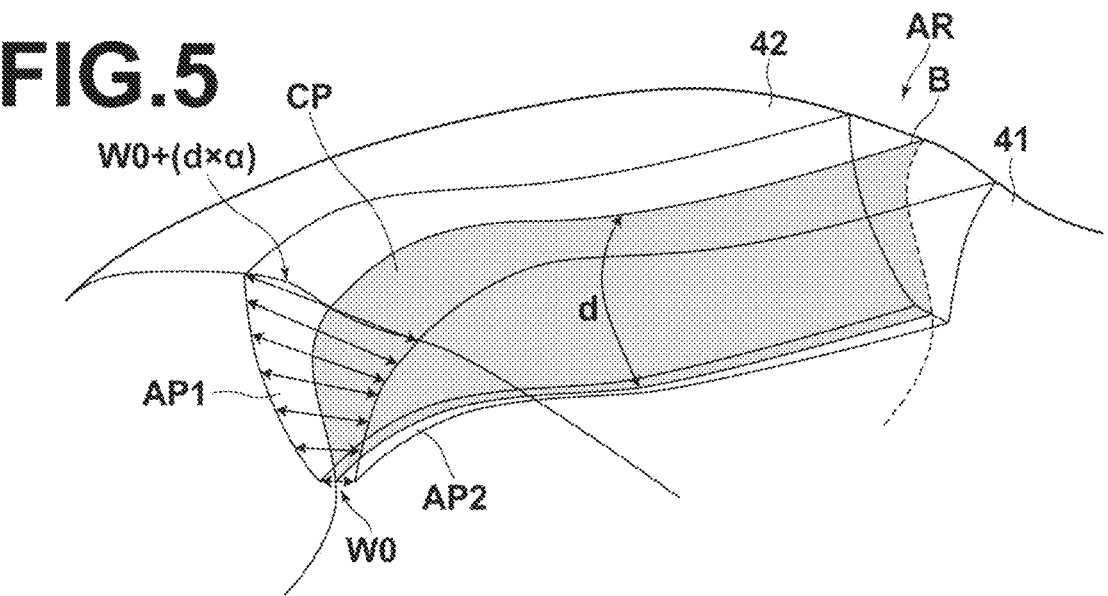
FIG. 5 is a diagram illustrating another example of setting a neighborhood region of a cutting surface.
Figure 6:
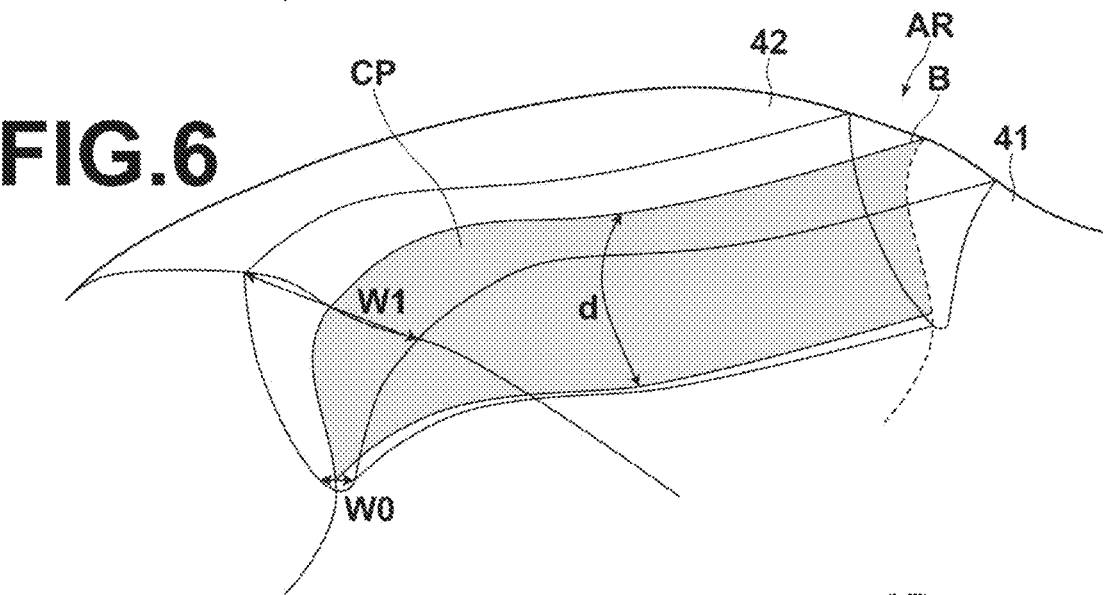
FIG. 6 is a diagram illustrating another example of setting a neighborhood region of a cutting surface.

Neighborhood region AR set by using the aforementioned methods has constant thickness W from the inner edge through the outer edge of cutting surface CP. However, it is not necessary that the neighborhood region setting unit 71 sets neighborhood region AR in this manner. For example, the neighborhood region setting unit 71 may set, as neighborhood region AR, a region the width of which in a direction perpendicular to cutting surface CP increases from the inner edge of cutting surface CP toward the outer edge of cutting surface CP. As illustrated in FIG. 5, the neighborhood region setting unit 71 may set, as neighborhood region AR, a region having first width W0 that has been set in advance in a direction perpendicular to cutting surface CP at the inner edge of cutting surface CP, and the width of which in a direction perpendicular to cutting surface CP increases from the inner edge of cutting surface CP toward the outer edge of cutting surface CP at ratio α that has been set in advance. Alternatively, as illustrated in FIG. 6, the neighborhood region setting unit 71 may set, as neighborhood region AR, a region having first width W0 that has been set in advance in a direction perpendicular to cutting surface CP at the inner edge of cutting surface CP and second width W1 (>W0) that has been set in advance in a direction perpendicular to cutting surface CP at the outer edge of cutting surface CP.

FIGS. 3 through 6 illustrate cases in which neighborhood region AR has an arbitrary thickness from cutting surface CP toward both of the excision region 41 side and the non-excision 42 side. Alternatively, neighborhood region AR may be a region having an arbitrary thickness from cutting surface CP only toward the excision region 41 side, or only toward the non-excision 42 side. In this case, neighborhood region AR may be obtained, for example, by obtaining the product, which is an intersection area, of the neighborhood region AR having the arbitrary thickness toward both sides, and which was obtained by using the aforementioned method, and the excision region 41 or the non-excision region 42.

Figure 7:
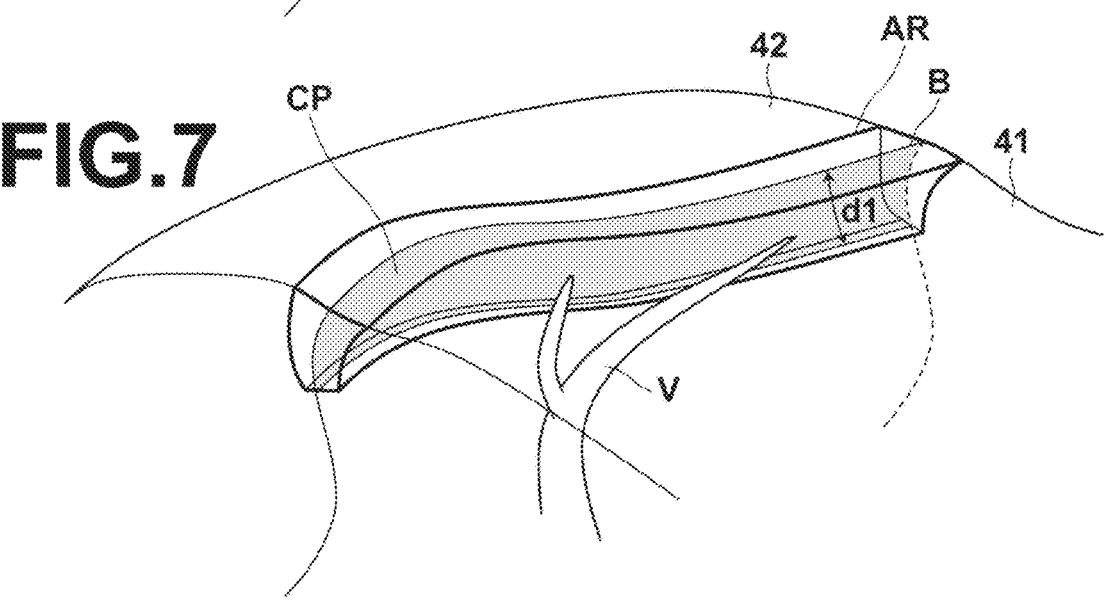
FIG. 7 is a diagram for explaining a visible range of a blood vessel region according to setting of a depth of cutting.
Figure 8:
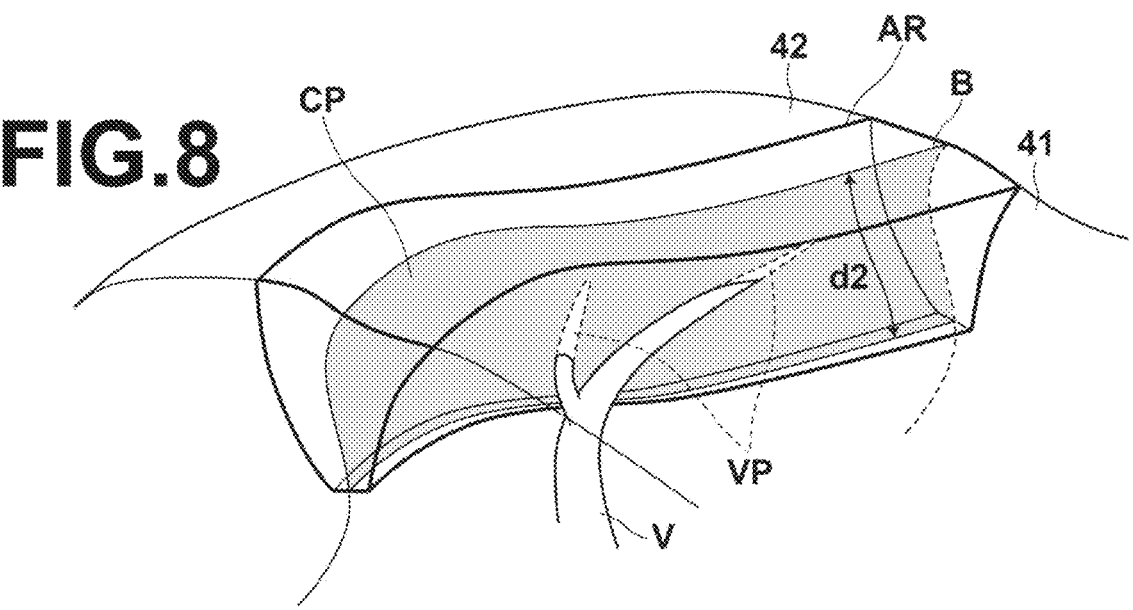
FIG. 8 is a diagram for explaining a visible range of a blood vessel region according to setting of a depth of cutting.

FIG. 7 and FIG. 8 illustrate positional relationships between neighborhood region AR and blood vessel region V when different depths d1 and d2 (>d1) of cutting are set, respectively. FIG. 7 illustrates a case in which blood vessel region V is not included in neighborhood region AR, and blood vessel region V is not visualized. FIG. 8 illustrates a case in which a portion of blood vessel region V is included in neighborhood region AR, and the portion of blood vessel region V is visualized. As illustrated in FIGS. 7 and 8, a visualized range of blood vessel region V changes when the depth of cutting changes.

Figure 9:
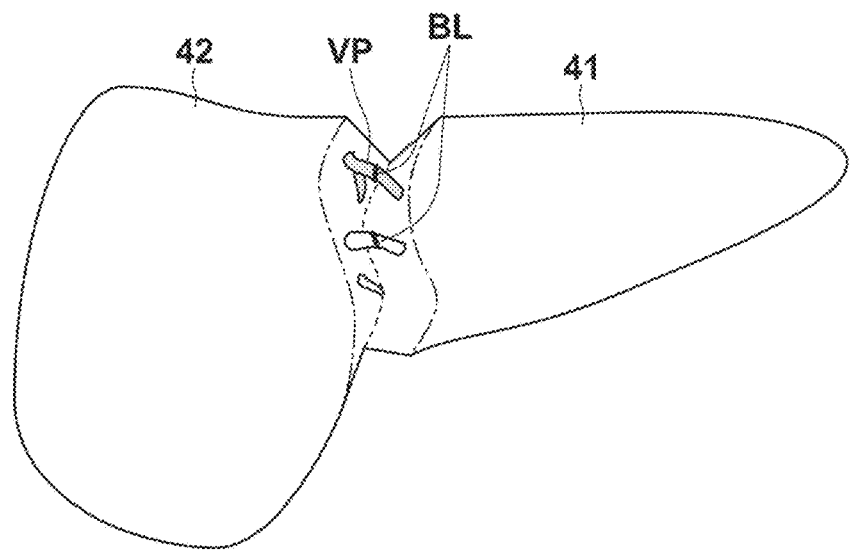
FIG. 9 is a diagram illustrating an example of a simulation image.
Figure 10:
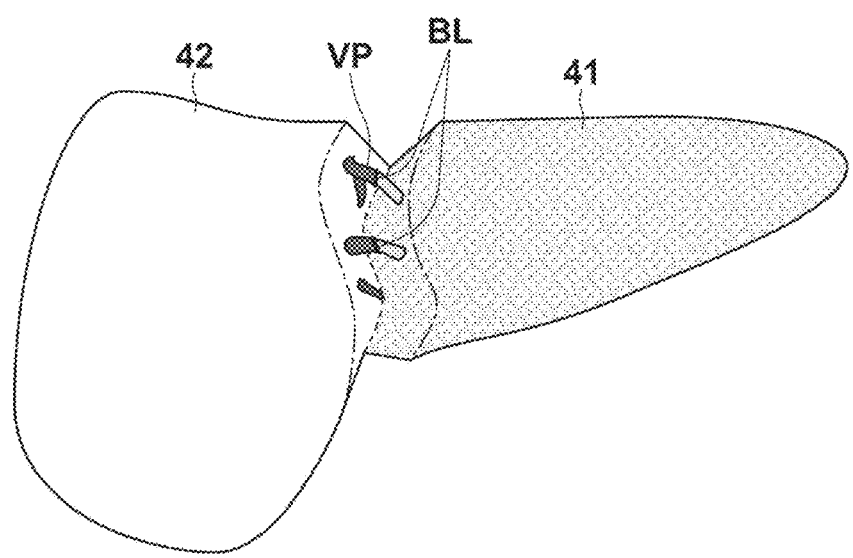
FIG. 10 is a diagram illustrating another example of a simulation image.

The simulation image generation unit 72 generates simulation images based on information about neighborhood region AR that has been set by the neighborhood region setting unit 71, for example, as illustrated in FIG. 9 and FIG. 10. The simulation images represent an organ in such a manner that only partial blood vessel region VP that is present in neighborhood region AR of cutting surface CP in the whole blood vessel region V of the organ is visually recognizable. For example, first, an opacity value and color information of R, G and B are given to each voxel constituting a three-dimensional image. At this time, opacity values of 80 to 100% (opacity values higher than opacity values given to a partial parenchyma region) are given only to voxels constituting partial blood vessel region VP present in neighborhood region AR in the whole blood vessel region V of the organ. Meanwhile, opacity values of 0 to 20% (opacity values lower than the opacity values given to partial blood vessel region VP) are given to voxels constituting the partial parenchyma region present in neighborhood region AR. Further, when a tumor region is present in neighborhood region AR, opacity values of 80 to 100% (opacity values higher than the opacity values given to the partial parenchyma region) are given also to voxels constituting the tumor region. Further, a volume rendering image representing the organ is generated, as the simulation image, by performing ray-casting from a viewpoint.

When the simulation image generation unit 72 generates the simulation image, the simulation image generation unit 72 may generate a simulation image, in which the excision region 41 side and the non-excision region 42 side are displayed in a distinguishable manner from each other, as illustrated in FIG. 10, by giving different color information to voxels present toward the excision region 41 side of boundary surface B from color information given to voxels present toward the non-excision region 42 side of boundary surface B and by performing the ray casting. Further, color information corresponding to a distance from boundary surface B to each voxel may be given to each voxel present toward the excision region 41 side and each voxel present toward the non-excision region 42 side. Further, as illustrated in FIG. 9 and FIG. 10, intersection line BL of partial blood vessel region VP and boundary surface B may be drawn in the simulation image. Further, as illustrated in FIG. 9, different colors may be given to the portal vein and the hepatic veins to make them distinguishable from each other.

The display control unit 80 displays the simulation image generated by the image generation unit 70 on the display 3.

FIG. 11 is a flow chart for explaining the action of a surgery assistance system according to an embodiment of the present invention. The action of the surgery assistance system will be described with reference to this flow chart. In the surgery assistance system according to an embodiment of the present invention, first, a selection menu is displayed on the display 3. When selection of a surgery assistance function according to an embodiment of the present invention at the selection menu is detected, a list of ID's of patients to be examined is displayed on the display 3. Further, the ID of a patient to be examined who is a target of surgery is selected from the list of ID's of patients to be examined displayed on the display 3. When the surgery assistance apparatus 1 detects a selection operation by the user, the image obtainment unit 10 in the surgery assistance apparatus 1 obtains a three-dimensional image related to the selected patient to be examined (S1).

Next, the three-dimensional image obtained by the image obtainment unit 10 is input to the organ region extraction unit 20. The organ region extraction unit 20 extracts an organ region from the input three-dimensional image (S2). Next, the organ region extracted by the organ region extraction unit 20 is input to the blood vessel region extraction unit 30, and the blood vessel region extraction unit 30 extracts blood vessel region V from the organ region (S3). Meanwhile, the organ region extracted by the organ region extraction unit 20 is input also to the excision region determination unit 40. The excision region determination unit 40 extracts an abnormal region from the organ region, and identifies a portion of blood vessel region V related to the extracted abnormal region. Further, the excision region determination unit 40 determines, as an excision region 41, a dominated region in the organ dominated by the identified portion of blood vessel region V. Further, the excision region determination unit 40 determines, as a non-excision region 42, the organ region other than the determined excision region 41 (S4).

Further, a setting screen for making a user set depth d of cutting is displayed on the display 3. When the input receiving unit 50 receives an input of setting depth d of cutting in the displayed screen by the user using the input device 4, such as a mouse (S5), the cutting surface setting unit 60 sets, as cutting surface CP, a portion of boundary surface B within depth d of cutting along boundary surface B from an outer edge of boundary surface B toward the inside, and boundary surface B being between the excision region 41 and the non-excision region 42 in the organ region (S6). Here, the cutting surface setting unit 60 generates a distance map in which distances are related to all the voxels constituting boundary surface B, respectively, by obtaining a shortest distance along boundary surface B from a voxel constituting the outer edge of boundary surface B for each of the voxels constituting boundary surface B. Then, the cutting surface setting unit 60 identifies, by referring to the generated distance map, a set of voxels related to distances that are less than or equal to depth d of cutting that has been input by the user and received at the input receiving unit 50, among all the voxels constituting boundary surface B. Further, the cutting surface setting unit 60 sets the identified set of voxels, as cutting surface CP.

Next, the image generation unit 70 generates a simulation image from the three-dimensional image obtained by the image obtainment unit 10 (S7). The simulation image represents an organ in such a manner that only partial blood vessel region VP that is present in neighborhood region AR of cutting surface CP in the whole blood vessel region V of the organ is visually recognizable. The image generation unit 70 sets, as neighborhood region AR of cutting surface CP, a region with an arbitrary thickness from cutting surface CP toward one of the excision region 41 side and the non-excision 42 side, or toward both of the excision region 41 side and the non-excision 42 side. Further, the image generation unit 70 generates a volume rendering image representing the organ in which the parenchyma region in the organ that is present in set neighborhood region AR is not displayed or is displayed semi-transparently. Further, the simulation image representing the organ, and which has been generated by the image generation unit 70, is output to the display control unit 80. The display control unit 80 displays the input simulation image on the display 3 (S8).

Next, whether an instruction to end the surgery assistance function according to an embodiment of the present invention is present or not is detected (S9). If the instruction to end the surgery assistance function is not detected, the process goes back to step S5. If the instruction to end the surgery assistance function is detected, the process ends here. When the instruction to end the surgery assistance function is not detected, if an input of changing depth d of cutting by the user is received at the input receiving unit 50, the cutting surface setting unit 60 updates setting of cutting surface CP by using the changed depth d of cutting. Further, the image generation unit 70 updates neighborhood region AR of cutting surface CP in response to the update of cutting surface CP, and generates a new simulation image. The display control unit 80 displays the generated image on the display 3.

The surgery assistance system according to the embodiment of the present invention is configured as described above. Therefore, when the surgery assistance system generates, from a three-dimensional image of an organ in which an excision region 41 has been identified, an image representing the organ in such a manner that blood vessel region V in the organ is visually recognizable, the system receives an input specifying a depth of cutting. Further, the system determines, as cutting surface CP, a portion of boundary surface B within the specified depth of cutting along boundary surface B from an outer edge of boundary surface B toward an inside, and boundary surface B being between the excision region 41 and a non-excision region 42, which is a region other than the excision region, in the organ. Further, the system generates, from the three-dimensional image, the image representing the organ in such a manner that only partial blood vessel region VP, which is present in neighborhood region AR of cutting surface CP in blood vessel region V of the organ, is visually recognizable. Therefore, when observation is performed by paying attention to the course of blood vessels in the neighborhood of cutting surface CP, it is possible to provide an image appropriate for observation in which a limited part of the whole blood vessel region V to which attention is paid in observation is displayed.

In the aforementioned embodiment, a case in which the organ region extraction unit 20, the blood vessel region extraction unit 30 and the excision region determination unit 40 are provided in the surgery assistance apparatus 1, and each processing of organ region extraction, blood vessel region extraction and excision region determination is performed in the surgery assistance apparatus 1 has been described. However, when each of these kinds of processing has been already performed by another computer or the like, and the result of processing is retrievable, it is not always necessary that the organ region extraction unit 20, the blood vessel region extraction unit 30 and the excision region determination unit 40 are included in the configuration.

In the aforementioned embodiment, processing when the target organ is the liver was mainly described. However, the organ in the present invention is not limited to the liver. The present invention is applicable to assistance in surgery of other organs, such as the lungs.

What is claimed is:

1. A surgery assistance apparatus comprising:
   a memory; and
   a processor coupled to the memory, the processor being configured to execute a process including:
   receiving an input specifying a depth of cutting in a three-dimensional image comprising voxels and of an organ in which an excision region has been identified;
   computing a first distance map specifying distances along a boundary surface in the three-dimensional image and from an outer edge of the boundary surface toward an inside of the organ;
   determining based on the first distance map, a portion of the boundary surface within the specified depth of cutting along the boundary surface from an outer edge of the boundary surface toward an inside of the organ as a cutting surface, and the boundary surface being between the excision region and a non-excision region that is a region other than the excision region, in the organ;
   specifying, for each of a plurality of locations associated with one or more voxels on the cutting surface, a width along the direction orthogonal to the cutting surface from said respective locations that depends on a distance at said respective locations from the outer edge of the boundary surface indicated by the first distance map and setting a neighborhood region, subsequent to determining the cutting surface, around the cutting surface that extends to the specified width; and
   generating, from the three-dimensional image, an image representing the organ in such a manner that only a part of a blood vessel region that is included in the neighborhood region of the cutting surface is visually recognizable.

2. The surgery assistance apparatus, as defined in claim 1, wherein the neighborhood region of the cutting surface is a region, wherein the specified width of the region along the direction orthogonal to the cutting surface increases from an inner edge of the cutting surface toward an outer edge of the cutting surface.

3. The surgery assistance apparatus, as defined in claim 2, wherein the neighborhood region of the cutting surface has a first width that has been specified in advance along the direction orthogonal to the cutting surface at the inner edge of the cutting surface and a second width that has been specified in advance along the direction orthogonal to the cutting surface at the outer edge of the cutting surface.

4. The surgery assistance apparatus, as defined in claim 3, wherein the process further includes:
receiving an input of specifying the first width,
wherein the neighborhood region of the cutting surface has the first width that has been specified along the direction orthogonal to the cutting surface at the inner edge of the cutting surface.

5. The surgery assistance apparatus, as defined in claim 2, wherein the neighborhood region of the cutting surface has a first width that has been specified in advance along the direction orthogonal to the cutting surface at the inner edge of the cutting surface, and the first specified width of which along the direction orthogonal to the cutting surface increases from the inner edge of the cutting surface toward the outer edge of the cutting surface at a ratio that has been set in advance.

6. The surgery assistance apparatus, as defined in claim 5, wherein the process further includes:
receiving an input of specifying the first width,
wherein the neighborhood region of the cutting surface has the first width that has been specified along the direction orthogonal to the cutting surface at the inner edge of the cutting surface.

7. The surgery assistance apparatus, as defined in claim 1, wherein the neighborhood region of the cutting surface is present only toward the excision region from the cutting surface.

8. The surgery assistance apparatus, as defined in claim 1, wherein the neighborhood region of the cutting surface is present only toward the non-excision region from the cutting surface.

9. The surgery assistance apparatus, as defined in claim 1, wherein the manner that only the part of the blood vessel region is visually recognizable is a manner that a parenchyma region in the organ present in the neighborhood region of the cutting surface is not displayed or is displayed at a lower opacity value than the opacity value of the part of the blood vessel region.

10. A surgery assistance method comprising:
receiving an input specifying a depth of cutting in a three-dimensional image comprising voxels and of an organ in which an excision region has been identified;
computing a first distance map specifying distances along a boundary surface in the three-dimensional image and from an outer edge of the boundary surface toward an inside of the organ;
determining, based on the first distance map, a portion of the boundary surface within the specified depth of cutting along the boundary surface from an outer edge of the boundary surface toward an inside of the organ as a cutting surface, and the boundary surface being between the excision region and a non-excision region that is a region other than the excision region, in the organ; and
specifying, for each of a plurality of locations associated with one or more voxels on the cutting surface, a width along the direction orthogonal to the cutting surface from said respective locations that depends on a distance at said respective locations from the outer edge of the boundary surface indicated by the first distance map and setting a neighborhood region, subsequent to determining the cutting surface, around the cutting surface that extends to the specified width; and
generating, from the three-dimensional image, an image representing the organ in such a manner that only a part of a blood vessel region that is included in the neighborhood region of the cutting surface is visually recognizable.

11. The surgery assistance method, as defined in claim 10, wherein the neighborhood region of the cutting surface is a region, wherein the specified width of the region along the direction orthogonal to the cutting surface increases from an inner edge of the cutting surface toward the outer edge of the cutting surface.

12. The surgery assistance method, as defined in claim 11, wherein the neighborhood region of the cutting surface has a first width that has been specified in advance along the direction orthogonal to the cutting surface at the inner edge of the cutting surface and a second width that has been specified in advance along the direction orthogonal to the cutting surface at the outer edge of the cutting surface.

13. The surgery assistance method, as defined in claim 11, wherein the neighborhood region of the cutting surface has a first width that has been specified in advance along the direction orthogonal to the cutting surface at the inner edge of the cutting surface, and the first specified width of which along the direction orthogonal to the cutting surface increases from the inner edge of the cutting surface toward the outer edge of the cutting surface at a ratio that has been set in advance.

14. A non-transitory computer-readable recording medium having stored therein a surgery assistance program for executing the following functions:
receiving an input specifying a depth of cutting in the three-dimensional image comprising voxels and of an organ in which an excision region has been identified;
computing a first distance map specifying distances along a boundary surface in the three-dimensional image and from an outer edge of the boundary surface toward an inside of the organ;
determining, based on the first distance map, a portion of the boundary surface within the specified depth of cutting along the boundary surface from an outer edge of the boundary surface toward an inside of the organ, and the boundary surface being between the excision region and a non-excision region that is a region other than the excision region, in the organ; and
specifying, for each of a plurality of locations associated with one or more voxels on a cutting surface, a width along the direction orthogonal to the cutting surface from said respective locations that depends on a distance at said respective locations from the outer edge of the boundary surface indicated by the first distance map and setting a neighborhood region, subsequent to determining the cutting surface, around the cutting surface that extends to the specified width; and
generates, from the three-dimensional image, an image representing the organ in such a manner that only a part of a blood vessel region that is included in the neighborhood region of the cutting surface is visually recognizable.

15. The non-transitory computer-readable recording medium, as defined in claim 14, wherein the neighborhood region of the cutting surface is a region, wherein the specified width of the region along the direction orthogonal to the cutting surface increases from an inner edge of the cutting surface toward the outer edge of the cutting surface.

16. The non-transitory computer-readable recording medium, as defined in claim 15, wherein the neighborhood region of the cutting surface has a first width that has been specified in advance along the direction orthogonal to the cutting surface at the inner edge of the cutting surface and a second width that has been specified in advance along the direction orthogonal to the cutting surface at the outer edge of the cutting surface.

17. The non-transitory computer-readable recording medium, as defined in claim 15, wherein the neighborhood region of the cutting surface has a first width that has been specified in advance along the direction orthogonal to the cutting surface at the inner edge of the cutting surface, and the first specified width of which along the direction orthogonal to the cutting surface increases from the inner edge of the cutting surface toward the outer edge of the cutting surface at a ratio that has been set in advance.

\* \* \* \* \*